(12) United States Patent
Stolarski et al.

(10) Patent No.: US 7,907,994 B2
(45) Date of Patent: Mar. 15, 2011

(54) AUTOMATED PACE-MAPPING FOR IDENTIFICATION OF CARDIAC ARRHYTHMIC CONDUCTIVE PATHWAYS AND FOCI

(75) Inventors: Silvia Stolarski, Haifa (IL); Aharon Turgeman, Zichron Ya'acov (IL); Meir Bar-Tal, Zichron Ya'acov (IL); Ronnie Abbo, Givat Ada (IL); Assaf Govari, Haifa (IL); Yaron Ephrath, Karkur (IL); Andres Claudio Altmann, Haifa (IL); Dror Levy, Kiriat Tivon (IL)

(73) Assignee: Biosense Webster, Inc., Diamond Bar, CA (US)

( * ) Notice: Subject to any disclaimer, the term of this patent is extended or adjusted under 35 U.S.C. 154(b) by 490 days.

(21) Appl. No.: 11/970,803

(22) Filed: Jan. 8, 2008

(65) Prior Publication Data

US 2008/0188765 A1 Aug. 7, 2008

Related U.S. Application Data

(60) Provisional application No. 60/884,493, filed on Jan. 11, 2007.

(51) Int. Cl.
*A61B 5/04* (2006.01)
(52) U.S. Cl. ...................................... 600/515
(58) Field of Classification Search .................. 600/508, 600/515, 519; 606/32–34, 41
See application file for complete search history.

(56) References Cited

U.S. PATENT DOCUMENTS

| | | | |
|---|---|---|---|
| 5,443,489 A | 8/1995 | Ben-Haim | |
| 5,450,846 A * | 9/1995 | Goldreyer | 600/374 |
| 5,546,951 A | 8/1996 | Ben-Haim | |
| 5,609,157 A | 3/1997 | Panescu et al. | |
| 5,738,096 A | 4/1998 | Ben-Haim | |
| 6,226,542 B1 | 5/2001 | Reisfeld | |
| 6,301,496 B1 | 10/2001 | Reisfeld | |
| 6,332,089 B1 | 12/2001 | Acker et al. | |
| 6,618,612 B1 | 9/2003 | Acker et al. | |
| 6,669,692 B1 | 12/2003 | Nelson et al. | |
| 6,690,963 B2 | 2/2004 | Ben-Haim et al. | |
| 6,799,064 B1 * | 9/2004 | Hassett | 600/374 |
| 6,847,839 B2 | 1/2005 | Ciaccio et al. | |
| 6,892,091 B1 * | 5/2005 | Ben-Haim et al. | 600/509 |
| 2002/0087089 A1 | 7/2002 | Ben-Haim | |
| 2003/0120150 A1 | 6/2003 | Govari | |
| 2004/0068178 A1 | 4/2004 | Govari | |
| 2004/0102769 A1 | 5/2004 | Schwartz et al. | |
| 2004/0147920 A1 | 7/2004 | Keidar | |
| 2005/0099290 A1 | 5/2005 | Govari | |
| 2008/0097537 A1 * | 4/2008 | Duann et al. | 607/14 |

FOREIGN PATENT DOCUMENTS

| WO | WO 96/05768 A1 | 2/1996 |
|---|---|---|
| WO | WO 96/32897 | 10/1996 |
| WO | WO 2005/113057 | 12/2005 |
| WO | WO 2006/044699 | * 4/2006 |

* cited by examiner

*Primary Examiner* — Carl H Layno
*Assistant Examiner* — Brian T Gedeon
(74) *Attorney, Agent, or Firm* — Louis J. Capezzuto

(57) ABSTRACT

Ventricular tachycardia signals are induced in a living subject. Pace-mapped signals are then obtained from multiple points within the ventricle, and automatically compared numerically with the induced signals. Recognition of a high degree of cross correlation between the induced signals and one or more of the pace-mapped signals identifies arrhythmogenic foci or pathways, which may then be ablated, so that the arrhythmia becomes non-inducible.

2 Claims, 13 Drawing Sheets

AUTOMATED PACE-MAPPING FOR IDENTIFICATION OF CARDIAC ARRHYTHMIC CONDUCTIVE PATHWAYS AND FOCI

CROSS-REFERENCE TO RELATED APPLICATIONS

This application claims the benefit of U.S. Provisional Application No. 60/884,493 filed Jan. 11, 2007, which is herein incorporated by reference.

BACKGROUND OF THE INVENTION

1. Field of the Invention

This invention relates to the diagnosis and treatment of cardiac arrhythmias. More particularly, this invention relates to the identification of arrhythmogenic foci associated with ventricular tachycardia.

2. Description of the Related Art

TABLE 1

| Acronyms and Abbreviations | |
|---|---|
| DAC | Digital-To-Analog Converter |
| ECG | Electrocardiogram |
| EEG | Electroencephalogram |
| FFT | Fast Fourier Transform |
| ICA | Independent Component Analysis |
| ICD | Intracardiac Device |
| IS | Induced Electrocardiographic Signals |
| Min-PML | Minimum Number of Leads |
| PCA | Principal Component Analysis |
| PM | Pace-Mapped Electrocardiographic Signals |
| PMCT | Pace-Mapped Correlation Threshold |
| QL | Qualifying Leads |
| VT | Ventricular Tachycardia |
| WOI | Window of Interest |

Cardiac arrhythmias such as ventricular tachycardia are an important cause of morbidity and death. Commonly assigned U.S. Pat. No. 5,546,951, and U.S. Pat. No. 6,690,963, both issued to Ben Haim; and PCT application WO 96/05768, all of which are incorporated herein by reference, disclose methods for sensing an electrical property of heart tissue, for example, local activation time, as a function of the precise location within the heart. Data are acquired with one or more catheters having electrical and location sensors in their distal tips, which are advanced into the heart. Methods of creating a map of the electrical activity of the heart based on these data are disclosed in commonly assigned U.S. Pat. No. 6,226,542, and U.S. Pat. No. 6,301,496, both issued to Reisfeld, which are incorporated herein by reference. As indicated in these patents, location and electrical activity is typically initially measured on about 10 to about 20 points on the interior surface of the heart. These data points are then generally sufficient to generate a preliminary reconstruction or map of the cardiac surface. The preliminary map is often combined with data taken at additional points in order to generate a more comprehensive map of the heart's electrical activity. Indeed, in clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Catheters containing position sensors may be used to determine the trajectory of points on the cardiac surface. These trajectories may be used to infer motion characteristics such as the contractility of the tissue. As disclosed in U.S. Pat. No. 5,738,096, issued to Ben Haim, and incorporated herein in its entirety by reference, maps depicting such motion characteristics may be constructed when the trajectory information is sampled at a sufficient number of points in the heart.

U.S. Pat. No. 6,847,839, issued to Ciaccio, et al., describes a method for identifying and localizing a reentrant circuit isthmus in a heart of a subject during sinus rhythm, including: a) receiving electrogram signals from the heart during sinus rhythm via electrodes; b) storing the electrogram signals; c) creating a map based on the electrogram signals; d) finding a center reference activation location on the map; e) defining measurement vectors originating from the center reference activation location; f) selecting from the measurement vectors a primary axis vector indicating a location of the reentrant circuit isthmus in the heart; g) finding threshold points of electrogram signals on the map; h) connecting the threshold points to form a polygon indicating a shape of the reentrant circuit isthmus in the heart.

SUMMARY OF THE INVENTION

Electrical activity at a point in the heart is typically measured by advancing a catheter containing an electrical sensor at or near its distal tip to that point in the heart, contacting the tissue with the sensor and acquiring data at that point. One drawback with mapping a cardiac chamber using a catheter containing only a single, distal tip electrode is the long period of time required to accumulate data on a point-by-point basis over the requisite number of points required for a detailed map of the chamber as a whole. Hence, patients with unstable ventricular tachycardia (VT) can not tolerate a mapping procedure that lasts long enough to produce an accurate activation map. Therefore, pace mapping, performed by conventional techniques, is the method used in such cases. This involves pacing the chamber at a relatively fast rate (typically, but not necessarily at the cycle length of the arrhythmia), then comparing a body surface 12-lead ECG during pacing to the ECG recorded during clinical arrhythmia, either induced or previously recorded.

Myocardial scars are known to be associated with arrhythmic conductive pathways and foci, e.g., reentrant foci, that are responsible for ventricular tachycardia. Currently, identification of such foci using the aforementioned mapping techniques is a long and tedious procedure, for example, involving visual comparisons between the complexes associated with clinical ventricular tachycardia and pace-mapped signals. Such foci have been the subject of some prior research.

After a patient has recovered from an episode of ventricular tachycardia, a cardiologist may perform an electrophysiological study in order to identify foci of the arrhythmia. During the study, a pacing catheter is introduced into the heart chamber and is operated to apply electrical stimulation pulses to the myocardium at different locations in an attempt to induce ventricular tachycardia. If pacing at a given site induces ventricular tachycardia or other arrhythmia, the arrhythmia is recorded and compared to the pacing from other sessions.

The VT-related patterns that are induced by electrophysiological pacing may be transient and difficult to identify. As a result, the job of searching for VT foci can be tedious and inaccurate, and it may be too difficult for less experienced cardiologists. In response to these difficulties, embodiments of the present invention provide methods that can be used to automate the detection of VT foci by numerically comparing the characteristic related ECG patterns, i.e., between the clinical arrhythmia and the pace mapping points.

According to disclosed embodiments of the invention, ventricular tachycardia signals are induced in a living subject. Pace-mapped signals are then obtained from multiple points within the ventricle, and automatically compared numerically with the induced signals. Recognition of a high degree of cross correlation between the induced signals and one or more of the pace-mapped signals identifies arrhythmogenic foci, which may then be ablated. Several mathematical techniques are employed to obtain the numerical comparisons and correlations.

An embodiment of the invention provides a computer-implemented method for locating an arrhythmogenic focus or pathway in a heart of a living subject, which is carried out by recording a reference set of electrocardiographic signals from the subject, stimulating the heart at multiple locations endocardially or epicardially, and while stimulating at the multiple locations, recording respective sets of pace-mapped electrocardiographic signals. The method is further carried out by correlating the sets of pace-mapped electrocardiographic signals with the reference set of electrocardiographic signals. Responsively to a determination that a correlation between one of the sets of pace-mapped electrocardiographic signals and the reference set of electrocardiographic signals meets a predefined criterion, the arrhythmogenic focus or pathway is identified as the respective location corresponding to the one pace-mapped set of pace-mapped electrocardiographic signals.

In one aspect of the method, the reference set of electrocardiographic signals and the sets of pace-mapped electrocardiographic signals are recorded remotely from an analysis location where the signals are correlated. The method includes transmitting at least one of the reference set of electrocardiographic signals and the sets of pace-mapped electrocardiographic signals to the analysis location.

According to an aspect of the method, the reference set of electrocardiographic signals is recorded using an implanted intracardiac device and is transmitted to the analysis location in realtime.

Yet another aspect of the method includes recording a historic set of electrocardiographic signals remotely from the analysis location, transmitting the historic set of electrocardiographic signals to the analysis location, and comparing the historic set of electrocardiographic signals with the reference set of electrocardiographic signals at the analysis location.

According to still another aspect of the method, the reference set of electrocardiographic signals is transmitted to the analysis location at least in part wirelessly.

In a further aspect of the method, correlating is performed by calculating respective numerical comparisons between the sets of pace-mapped electrocardiographic signals and the reference set of electrocardiographic signals, and calculating a correlation coefficient.

According to one aspect of the method, the criterion is met when the correlation coefficient exceeds a predefined value.

According to another aspect of the method, the sets of pace-mapped electrocardiographic signals and the reference set of electrocardiographic signals comprise 12-lead electrocardiograms, and the criterion is met when the correlation coefficient exceeds a pre-defined value in a predefined number of leads of the 12-lead electrocardiograms.

A further aspect of the method includes constructing a functional map of the heart in which a degree of correlation between the sets of pace-mapped electrocardiographic signals and the reference set of electrocardiographic signals are related to the multiple locations.

Yet another aspect of the method includes inducing ventricular tachycardia prior to recording the reference set of electrocardiographic signals.

An embodiment of the invention provides a computer-implemented method for locating an arrhythmogenic abnormality in a heart of a living subject, which is carried out by stimulating the heart at multiple locations endocardially or epicardially, and, recording respective sets of pace-mapped electrocardiographic signals. The method is further carried out by detecting an abnormal electrocardiographic signal pattern in the sets of pace-mapped electrocardiographic signals indicative of an arrhythmogenic focus or pathway, memorizing the pattern, and subsequently automatically identifying a new instance of the pattern when recording new electrocardiographic signals.

One aspect of the method includes adding the pattern to a library for use in subsequent automatic identifications of a new instance of the pattern.

An additional aspect of the method includes automatically identifying a new instance of the pattern by selecting a first time interval containing a pattern of interest in the new electrocardiographic signals, computing respective values of a characteristic of the new electrocardiographic signals in a plurality of time segments within the first time interval, concatenating the respective values to form a signature of the pattern of interest, and identifying a further occurrence of the pattern of interest in the new electrocardiographic signals during a second time interval by matching the new electrocardiographic signals in the second time interval to the signature.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the present invention. It will be apparent to one skilled in the art, however, that the present invention may be practiced without these specific details. In other instances, well-known circuits, control logic, and the details of computer program instructions for conventional algorithms and processes have not been shown in detail in order not to obscure the present invention unnecessarily.

Software programming code, which embodies aspects of the present invention, is typically maintained in permanent storage, such as a computer readable medium. In a client/server environment, such software programming code may be stored on a client or a server. The software programming code may be embodied on any of a variety of known media for use with a data processing system, such as a diskette, or hard drive, or CD-ROM. The code may be distributed on such media, or may be distributed to users from the memory or storage of one computer system over a network of some type to other computer systems for use by users of such other systems.

System Architecture

Figure 1:
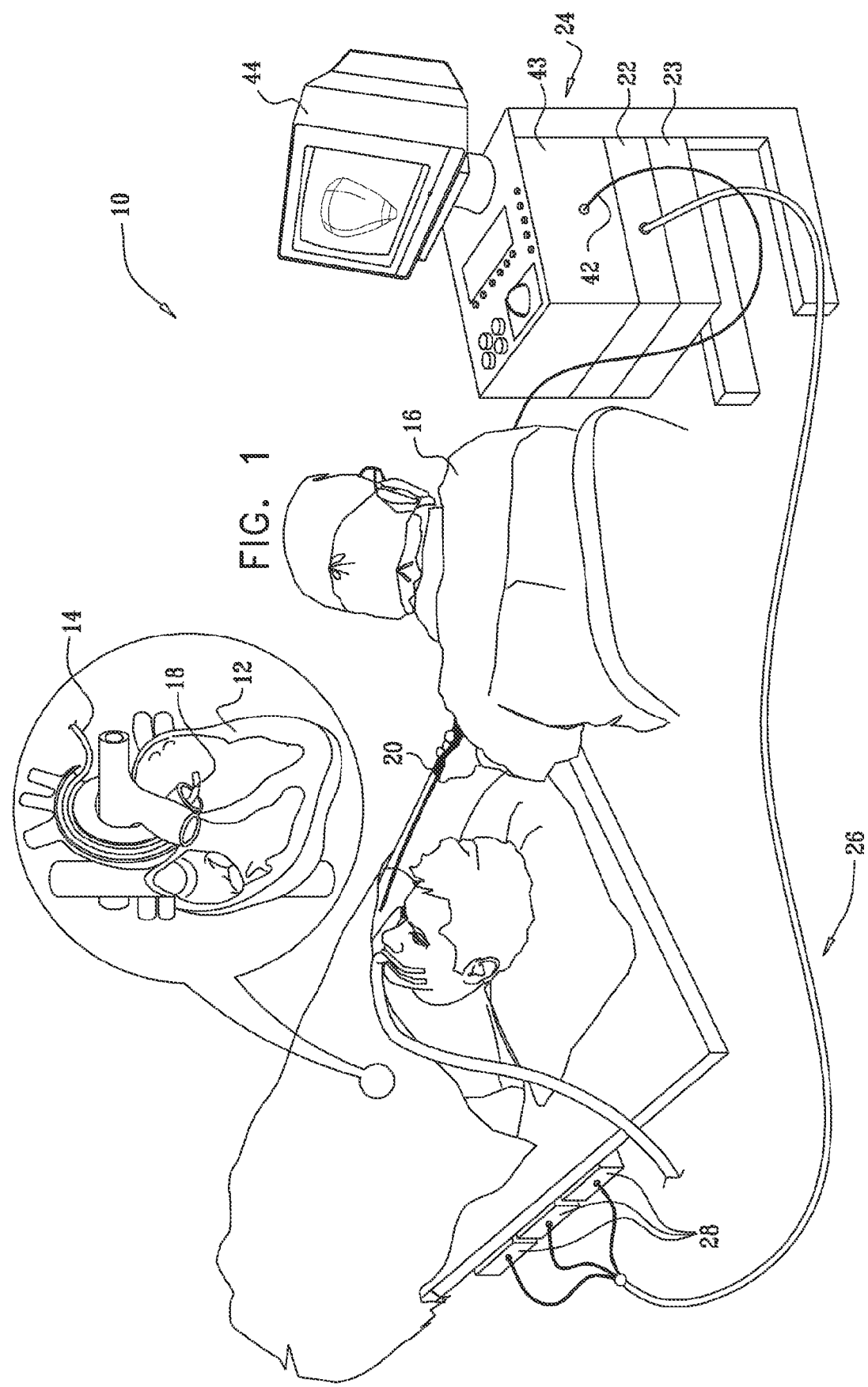
FIG. 1 is a pictorial illustration of a system that is adapted to detecting foci and conduction pathways responsible for ventricular tachycardia and performing ablative procedures on a heart of a living subject in accordance with a disclosed embodiment of the invention.

Turning now to the drawings, reference is initially made to FIG. 1, which is a pictorial illustration of a system 10 that is adapted to detecting areas in a heart 12 of a living subject that are associated with an arrhythmia and performing ablative procedures in accordance with a disclosed embodiment of the invention. The system comprises a probe, typically a catheter 14, which is percutaneously inserted by an operator 16, who is typically a physician, through the patient's vascular system into a chamber or vascular structure of the heart. The operator 16 brings the catheter's distal tip 18 into contact with the heart wall at a target site that is to be evaluated. Electrical activation maps are then prepared, according to the methods disclosed in the above-noted U.S. Pat. Nos. 6,226,542, and 6,301,496, and in commonly assigned U.S. Pat. No. 6,892,091, whose disclosure is herein incorporated by reference.

Areas determined to be abnormal by evaluation of the electrical maps can be ablated application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. Alternatively, other known methods of applying ablative energy can be used, e.g., ultrasound energy, as disclosed in U.S. Patent Application Publication No. 2004/0102769, whose disclosure is herein incorporated by reference. The principles of the invention are disclosed with respect to atrial complex fractionated electrograms, but can be applied to all heart chambers, to epicardial as well as endocardial approaches, and to mapping in sinus rhythm, and when many different cardiac arrhythmias are present.

The catheter 14 typically comprises a handle 20, having suitable controls on the handle to enable the operator 16 to steer, position and orient the distal end of the catheter as desired to the ablation. To aid the operator 16, the distal portion of the catheter 14 contains position sensors (not shown) that provide signals to a positioning processor 22, located in a console 24. The catheter 14, may be adapted, mutatis mutandis, from the ablation catheter described in commonly assigned U.S. Pat. No. 6,669,692, whose disclosure is herein incorporated by reference. The console 24 typically contains an ablation power generator 43. The console 24 also includes a processor 23 that performs signal correlation and analysis functions, which are described in further detail hereinbelow. In some embodiments, the processor 22 and processor 23 can be integrated into a single processor. The processor 23 can be realized as a general purpose computer.

The positioning processor 22 is an element of a positioning subsystem that measures location and orientation coordinates of the catheter 14. Throughout this patent application, the term "location" refers to the spatial coordinates of the catheter, and the term "orientation" refers to its angular coordinates. The term "position" refers to the full positional information of the catheter, comprising both location and orientation coordinates.

In one embodiment, the positioning subsystem 26 comprises a magnetic position tracking system that determines the position and orientation of the catheter 14. The positioning subsystem 26 generates magnetic fields in a predefined working volume its vicinity and senses these fields at the catheter. The positioning subsystem 26 typically comprises a set of external radiators, such as field generating coils 28, which are located in fixed, known positions external to the patient. The coils 28 generate fields, typically electromagnetic fields, in the vicinity of the heart 12.

In an alternative embodiment, a radiator in the catheter 14, such as a coil, generates electromagnetic fields, which are received by sensors (not shown) outside the patient's body.

Some position tracking systems that may be used for this purpose are described, for example, in the above-noted U.S. Pat. No. 6,690,963, and in commonly assigned U.S. Pat. Nos. 6,618,612 and 6,332,089, and U.S. Patent Application Publications 2004/0147920, and 2004/0068178, whose disclosures are all incorporated herein by reference. Although the positioning subsystem 26 shown in FIG. 1 uses magnetic fields, the methods described below may be implemented using any other suitable positioning subsystem, such as systems based on electromagnetic fields, acoustic or ultrasonic measurements.

Figure 2:
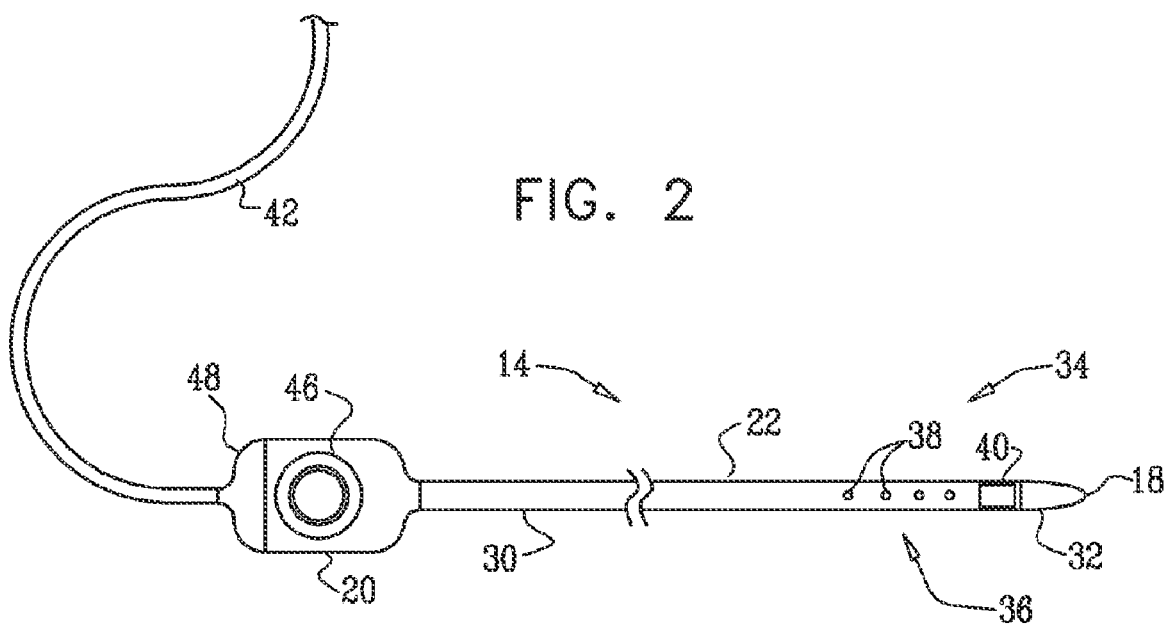
FIG. 2 is a diagram of an embodiment of the catheter for use in the system shown in FIG. 1.

Reference is now made to FIG. 2, which is a diagram of an embodiment of the catheter 14 for use in the system 10 (FIG. 1). The catheter 14 is a mapping and therapeutic delivery catheter for insertion into the human body, and into a chamber of the heart 12 (FIG. 1). The catheter shown is exemplary; many other types of catheters can be used as the catheter 14. The catheter 14 includes a body 30. An electrode 32 is at a distal portion 34 disposed for measuring the electrical properties of the heart tissue. The electrode 32 is also useful for sending electrical signals to the heart for diagnostic purposes, e.g., for electrical mapping, and/or for therapeutic purposes, e.g., for ablating defective cardiac tissue. The distal portion 34 further includes an array 36 of non-contact electrodes 38 for measuring far field electrical signals in the heart chamber. The array 36 is a linear array in that the non-contact electrodes 38 are linearly arranged along the longitudinal axis of the distal portion 34. The distal portion 34 further includes at least one position sensor 40 that generates signals used to determine the position and orientation of the distal tip 18 within the body. The position sensor 40 is preferably adjacent to the distal tip 18. There is a fixed positional and orientational relationship of the position sensor 40, the distal tip 18 and the electrode 32.

The position sensor 40 transmits, in response to the fields produced by the positioning subsystem 26 (FIG. 1), position-related electrical signals over a cable 42 running through the catheter 14 to the console 24. Alternatively, the position sensor 40 in the catheter 14 may transmit signals to the console 24 over a wireless link, as described in U.S. Patent Application Publication Nos. 2003/0120150 and 2005/0099290, the disclosures of which are herein incorporated by reference. The positioning processor 22 then calculates the location and orientation of the distal portion 34 of the catheter 14 based on the signals sent by the position sensor 40. The positioning processor 22 typically receives, amplifies, filters, digitizes, and otherwise processes signals from the catheter 14. The positioning processor 22 also provides a signal output to a display 44 that provides a visual indication of the position of the distal portion 34 and/or the distal tip 18 of the catheter 14 relative to the site chosen for ablation.

The handle 20 of the catheter 14 includes controls 46 to steer or deflect the distal portion 34, or to orient it as desired.

The cable 42 comprises a receptacle 48, which connects to the handle 20. The receptacle 48 is preferably configured to receive catheters of a specific model, and preferably includes user-evident identification of the specific model. One of the advantages in using the cable 42 is the ability to connect different models and types of catheters, such as those catheters having different handle configurations, to the same console 24 (FIG. 1). Another advantage in having a separate cable 42 is in the fact that it does not come into contact with patients, so that it is possible to reuse the cable 42 without sterilization. The cable 42 further contains one or more isolation transformers (not shown), which electrically isolate the catheter 14 from the console 24. The isolation transformers may be contained in the receptacle 48. Alternatively, isolation transformers may be contained in the system electronics of the console 24.

Referring again to FIG. 1, the system 10 can be realized as the above-mentioned CARTO XP EP Navigation and Ablation System, suitably modified to execute the procedures described herein.

General Operation

Figure 3:
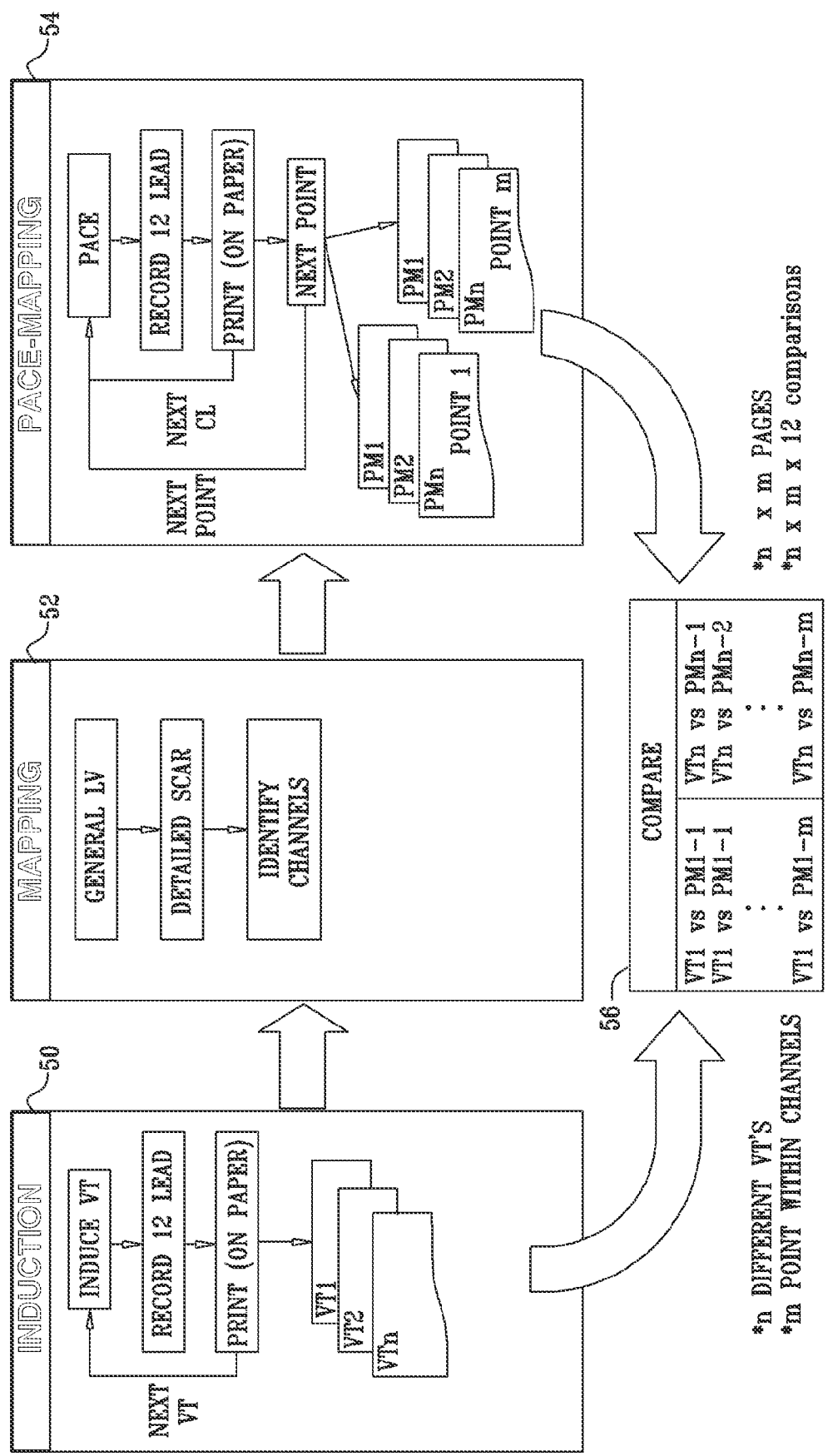
FIG. 3 is a diagram illustrating phases of a procedure for detecting arrhythmogenic foci and pathways associated with ventricular tachycardia in accordance with a disclosed embodiment of the invention.

Reference is now made to FIG. 3, which is a diagram illustrating phases of a procedure for detecting arrhythmogenic foci or pathways associated with ventricular tachycardia in accordance with a disclosed embodiment of the invention. In a first induction phase 50, ventricular tachycardia is induced (or observed without induction. Alternatively, traces may be imported by any suitable means, i.e., scanning, electronic transmission from other systems, which may be remote. Conventional 12-lead electrocardiographic signals are initially recorded and constitute a reference set of electrocardiographic signals. In a mapping phase 52, general mapping of the left ventricular anatomy and electrical characteristics are undertaken. This includes mapping of the chamber in order to identify possible locations of channels or focal points that may trigger the ventricular tachycardia (or other arrhythmia). This can be done by acquiring voltage maps or recording other electrical properties of the tissue, e.g., mid-diastolic potentials. Additionally or alternatively, the mapping may be carried out by merging or importing images that were acquired by other modalities.

In a pace-mapping phase 54, selected points are stimulated and electrocardiographic signals obtained to observe the effect of the stimulation. Then, in a comparison phase 56, some numerical measure of similarity is automatically determined between the electrocardiographic signals obtained in the induction phase 50 and the pace-mapping phase 54. In one embodiment, the measure of numerical correlation is derived from the covariance, (cov(X, Y)) of the two ECG signals (X, Y), as explained in further detail hereinbelow.

In another embodiment, a numerical method known as "principal component analysis" (PCA) is used to determine the correlation. This is described in further detail below. Briefly, the analysis is performed on a 12-lead body surface ECG recording of an induced signal. Three or four vectors are obtained, of which a combination can represent each of the induced signals recorded on a 12-lead body surface ECG. Similarity of the combination of the three or four vectors obtained in the principal component analysis (PCA) applied to the recorded induced signal can be used as a presentation of the 12-lead body surface ECG Pace Mapping. The normalized difference between the pace mapping and the represented pace mapping (using the vectors received from the principal component analysis on the induced signals recorded on the 12-lead body surface ECG) form the correlation values between corresponding leads.

Figure 4:
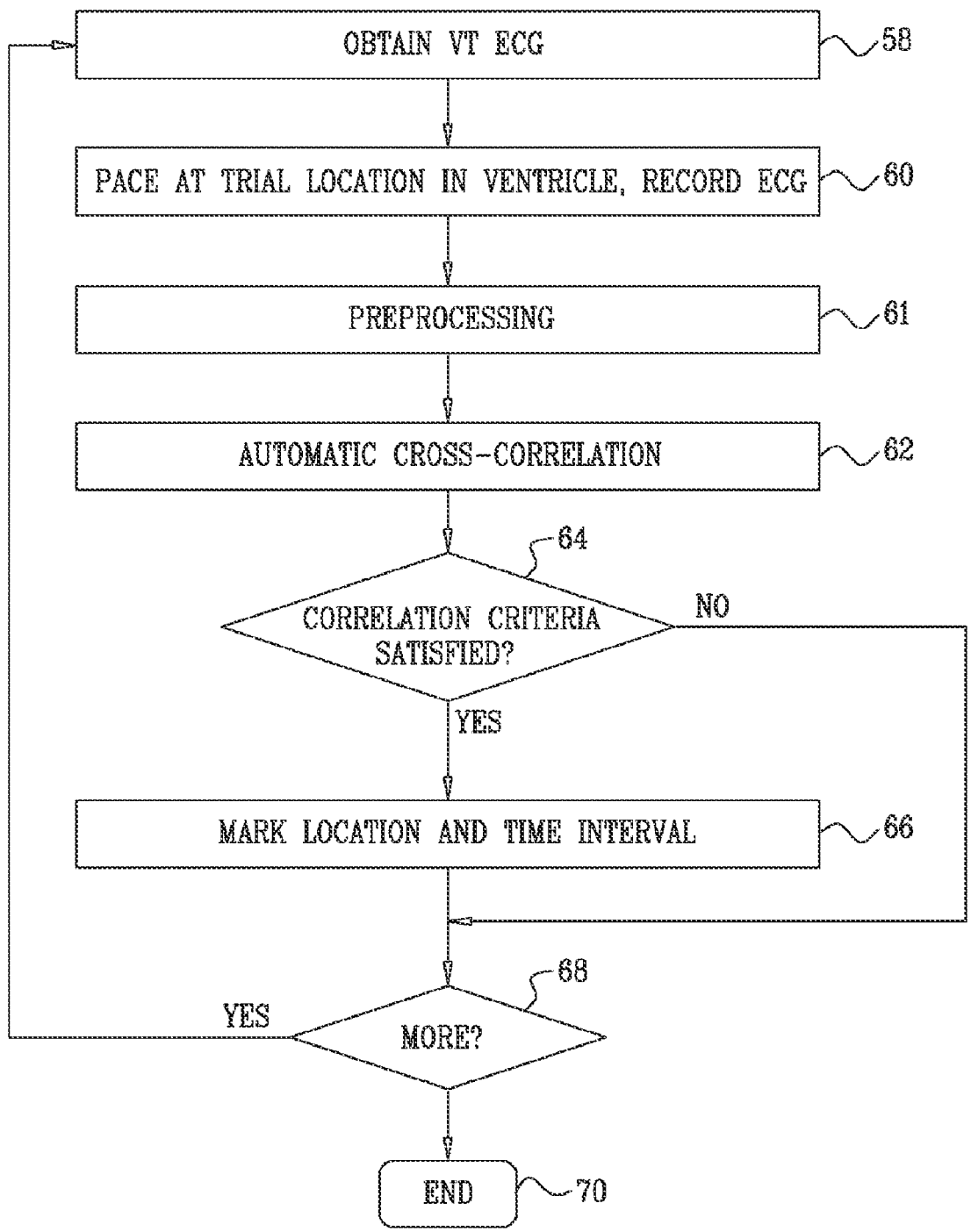
FIG. 4 is a flow chart of a method of detecting arrhythmogenic foci and pathways associated with ventricular tachycardia in accordance with a disclosed embodiment of the invention.

Reference is now made to FIG. 4, which is a flow chart of a method of automatically detecting and quantifying arrhythmogenic foci associated with ventricular tachycardia in accordance with a disclosed embodiment of the invention. The method can be used similarly in focal and reentry variants that are known to be associated with ventricular tachycardia. Alternatively, the method can be applied using entrainment stimulation. Indeed, the method can be applied to any arrhythmia that requires a comparison of signals for its evaluation. The order of the steps may be varied in practical embodiments. For example, recordings and correlation computations may be grouped.

At initial step 58 an ECG is obtained while the subject is experiencing ventricular tachycardia. This may be a clinical episode. Alternatively, ventricular tachycardia may be induced conventionally, e.g., pharmacologically or invasively, using a combination of fast and early stimuli. In order to obtain induced signals, or subsequent to recording spontaneous or pharmacologically induced ventricular tachycardia, a catheter, e.g., the catheter 14 (FIG. 2) is introduced into the ventricular chamber. An electrocardiographic tracing showing ventricular tachycardia is obtained, typically a 12-lead electrocardiogram. Conventional signal processing is applied to the electrocardiogram to obtain a digitized version. However, it will be apparent that the method is amenable to analog implementations. The following procedure is suitable for recording induced signals: record approximately 2.5 seconds of a 12-lead body surface ECG, independently of the status of any mapping catheters. A beat buffer is used for induced signals, i.e., the last two to three minutes are loop recorded and can be stopped at any time in order to catch a transient arrhythmia. The operator can select relevant ECG components to save as a template. After saving the chosen beat, the non-selected beats may be discarded. Template construction is described in further detail hereinbelow.

At step 60, pace mapping is performed at a trial location in the ventricle, and a digitized electrocardiographic record obtained.

Preprocessing is carried out next at step 61. First, the pacemaker spike is removed. This can be done using a median filter. The pacemaker spike, if left in place, can distort the correlations that are to be calculated, and thereby produce misleading results. Next, one of the leads is selected for evaluation. First, a maximum peak is identified. Then all other peaks having a magnitude that differs by at least 0.1 mm from that of the maximum are identified. Subsequent correlation analysis is carried out to obtain the best correlation in a window-of-interest (WOI) of the induced signal with a WOI in the pace-mapped signals around a found peak using a shift of +−20 ms. The procedure for calculating the correlation between induced signal (IS), which defines a template, and the pace-mapped signal (PM) is as follows:

1. A user-defined PM correlation threshold (between 0 and 1) and a user defined Minimum Number of Leads (Min-PML) are set. By default the PMCT=0.8, and Min-PML=10).
2. Each lead of the PM set is compared by cross correlation with the corresponding lead of the region of interest marked on all templates. All comparisons are at the same timing within the PM signal. This results in a set of 12 numbers for each PM-Template pair.
3. The IS has a defined WOI.
4. Calculate all the peaks in the PM in a selected lead.
5. Calculate the correlation between the IS with WOI and the PM with WOI defined around each peak with shift of +−20 ms.
6. Select the WOI with the best average correlation of all 12 leads.
7. Compare each lead's with the PMCT.
8. If at least Min-PML leads have correlations greater than PMCT, the average correlation us displayed, e.g., in a 3-dimensional map.

At step 62 correlation coefficients are automatically determined between the records obtained in the current iteration of steps 60, 61 and in initial step 58 as explained above. The correlation coefficient is given by:

$$\sigma_{x,y} = \frac{\text{Cov}(X, Y)}{\sigma_x \sigma_y},$$

where $$-1 \le \sigma_{xy} \le 1,$$

and $$\text{Cov}(X, Y) = \frac{1}{n}\sum_{i=1}^{n}(x_i - \mu_x)(y_i - \mu_y).$$

Control now proceeds to decision step 64, where it is determined if the correlation coefficients determined in step 62 satisfy pre-defined criteria. Details of this determination are presented in further detail hereinbelow.

If the determination at decision step 64 is affirmative, then control proceeds to step 66. The current location is marked as a possible arrhythmia triggering point or a possible point of a reentry path, and becomes a candidate for ablation. The time interval containing the correlated pattern is also marked.

After performing step 66, or if the determination at decision step 64 was negative, control proceeds to decision step 68, where it is determined if more locations in the ventricle are to be studied. Typically many points, typically about 24 or so are pace-mapped. Usually only a few of these become candidates for ablation. If the determination at decision step 68 is affirmative, then control returns to step 60.

If the determination at decision step 68 is affirmative, then control proceeds to final step 70. The locations identified at step 66 may be ablated if medically indicated.

Figure 5:
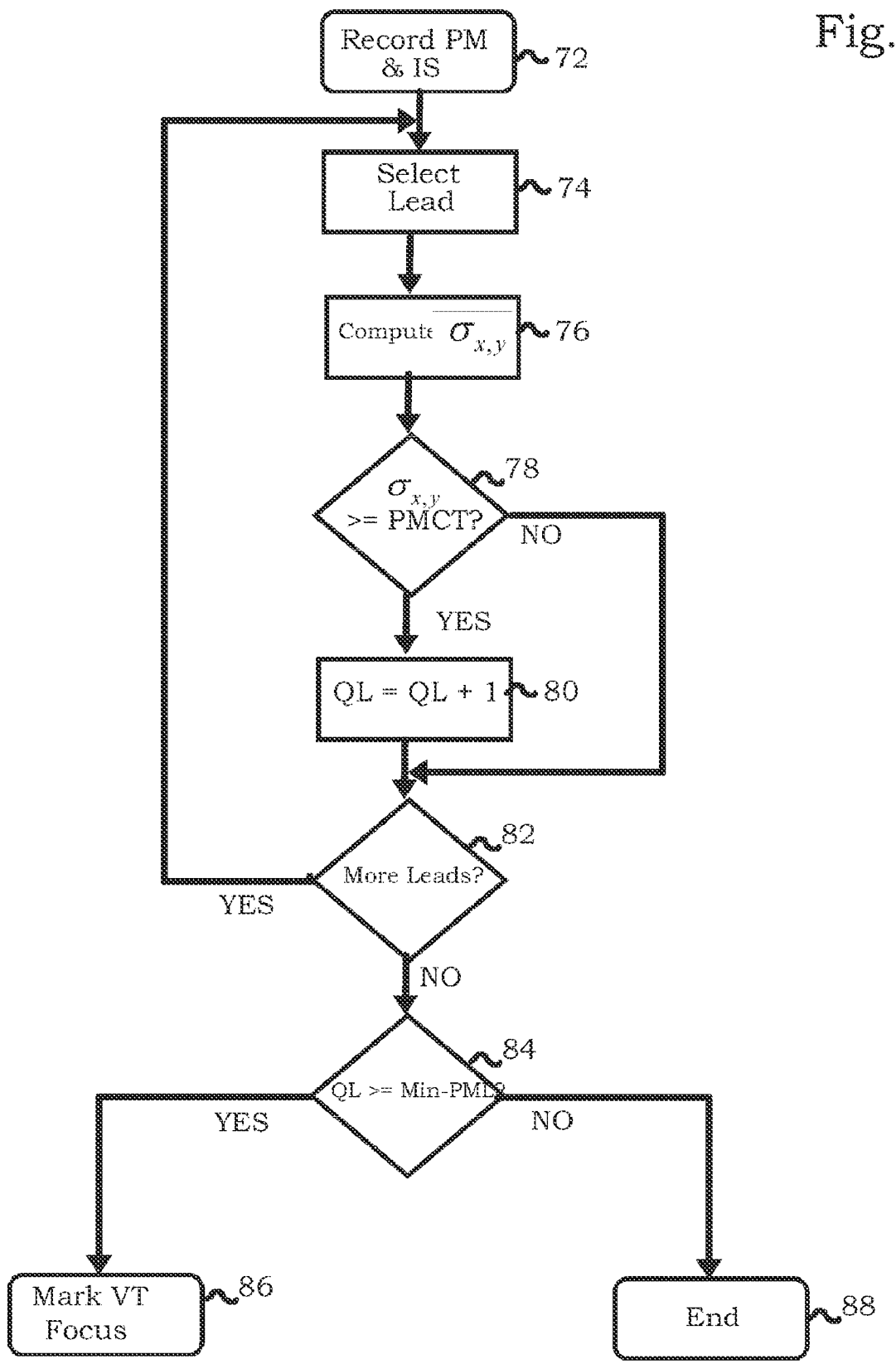
FIG. 5 is a detailed flow chart of a method for correlating pace-mapped electrocardiographic signals with induced electrocardiographic signals, in accordance with a disclosed embodiment of the invention.

Reference is now made to FIG. 5, which is a detailed flow chart of a method for correlating pace-mapped electrocardiographic signals (PM) with induced electrocardiographic signals (IS), in accordance with a disclosed embodiment of the invention. The method is essentially an elaboration of step 62 (FIG. 4). The description that follows applies to one IS template; however, the procedure is typically iterated for each IS template that was generated, i.e., for each existing clinical arrhythmia.

The process steps are shown in a particular linear sequence in FIG. 5 for clarity of presentation. However, it will be evident that the leads may be efficiently be evaluated in parallel, and the order of the steps may be varied in practice. At initial step 72, a digitized 12-lead induced electrocardiographic signal and a digitized 12-lead pace-mapped electrocardiographic signal are obtained as described above.

Each lead of a PM signal taken from a location is compared by cross correlation with the corresponding lead of the region of interest marked on a template. All comparisons are at the same timing within the PM signal. This results in a set of 12 numbers for each PM-Template pair compared.

Each lead's correlation with its corresponding lead is automatically evaluated numerically. At step 74, a lead is selected. Corresponding induced and pace-mapped signals recorded at this lead are used in step 76, where a correlation coefficient is computed as described above between the induced and pace-mapped signals.

Control now proceeds to decision step 78, where it is determined if a predefined pace-mapped correlation threshold (PMCT) was equaled or exceeded in the computation of step 76. Suitable values for the PMCT are about 0.9 or higher, and can be user defined.

If the determination at decision step 78 is affirmative, then control proceeds to step 80. The number of qualifying leads (QL) is incremented.

After performing step 80, or if the determination at decision step 78 is negative, control proceeds to decision step 82, where it is determined if more leads are to be evaluated.

If the determination at decision step 82 is affirmative, then control returns to step 74 for another iteration.

If the determination at decision step 82 is affirmative, then control proceeds to decision step 84, where it is determined whether the number of qualifying leads that have been accumulated in iterations of step 80 is at least a pre-defined minimum number of leads (Min-PML). Suitable values for Min-PML are about 10-11. These values can be modified by the user if desired.

If the determination at step decision step 84 is affirmative, then control proceeds to final step 86. The location associated with the PM signal is identified as an abnormal focus or pathway (channel) associated with ventricular tachycardia.

If the determination at decision step 84 is negative, then control proceeds to final step 88. The procedure has failed to associate the location associated with the PM signal as an abnormal focus or pathway associated with ventricular tachycardia.

Correlation Displays

Figure 6:
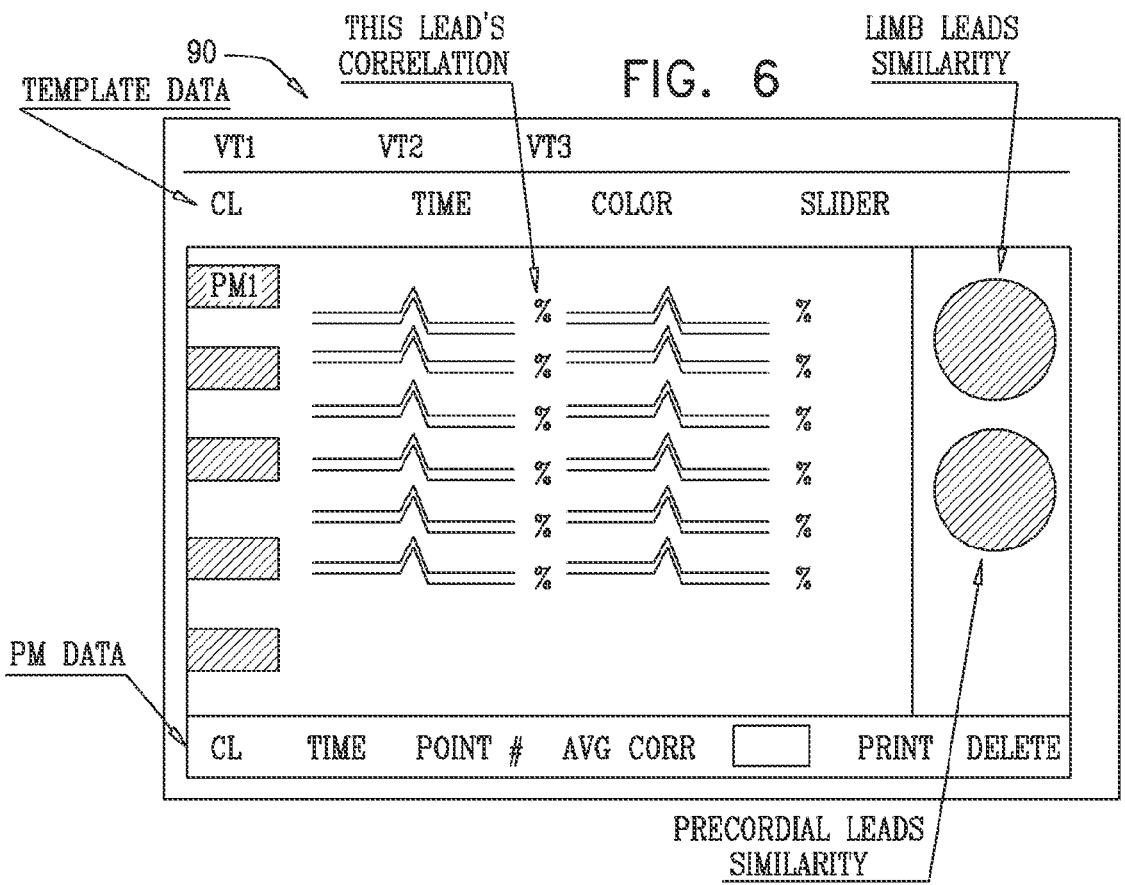
FIG. 6 illustrates a correlation display of electrocardiographic signals, in accordance with a disclosed embodiment of the invention.
Figure 9:
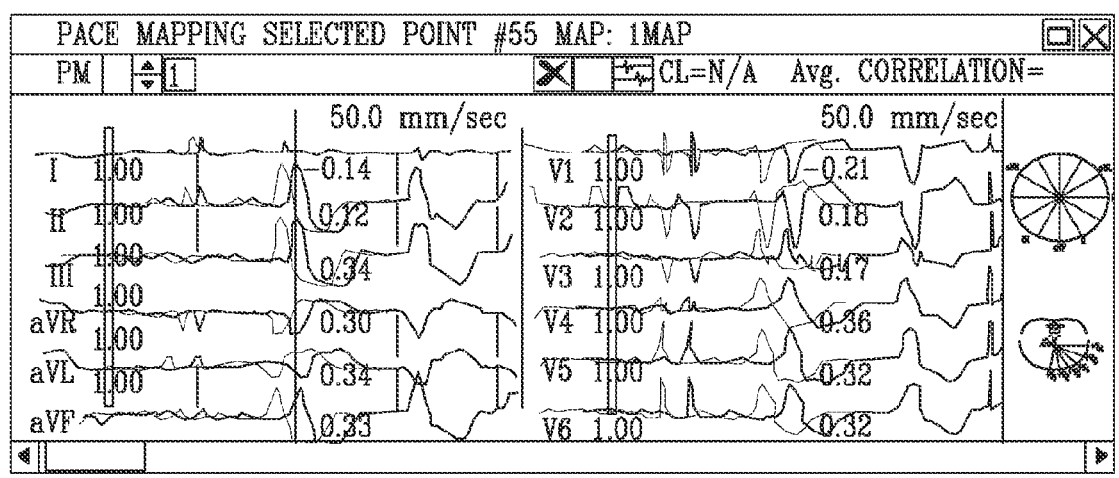
FIG. 9 is a series of tracings similar to FIG. 9, with superimposition of two series of signals, in accordance with a disclosed embodiment of the invention.

Correlation displays are generated indicating the correlation of pace-mapped ECG's with the ECG obtained in initial step 58 (FIG. 4). Reference is now made to FIG. 6, which illustrates a correlation display of electrocardiographic signals as a comparison window 90, in accordance with a disclosed embodiment of the invention. VT templates as shown on the window 90 are prepared for each type of VT complex recorded as an induced signal or spontaneously. In this example, a point PM1 has been selected. The display provides an option to scroll through all the PM's (whether their correlation is above or below the PMCT). For each lead, the correlation between the current template and the PM is displayed, as well as the average correlation for all leads. Colors differentiate IS from PM signals. By default, both signals are superimposed so that the portions of the signals on which the correlation was calculated are on top of each other. In one embodiment, it is possible to horizontally scroll the display of the PM signal, while the IS signal remains static. Thus, the PM to IS correlations, which appears to "slide" in real time, can be explored visually as shown in FIG. 9 (described below). Additionally any IS may be superimposed over another IS in order to assist the user in judging their similarity and validate the automatic assessment of template identification.

Once the user has released a scrolling control, all correlations for the current VT template-PM pair are recalculated and saved. Furthermore, the automatic correlation between the IS and PM signal may be recalculated at any time at the user's option.

Any VT template-PM pair having a negative correlation is automatically marked "not for display". This setting cannot be overridden unless the user has manually found a positive correlation. It is possible to change the time scale in a window. Any such change affects all leads at the same time.

Figure 7:
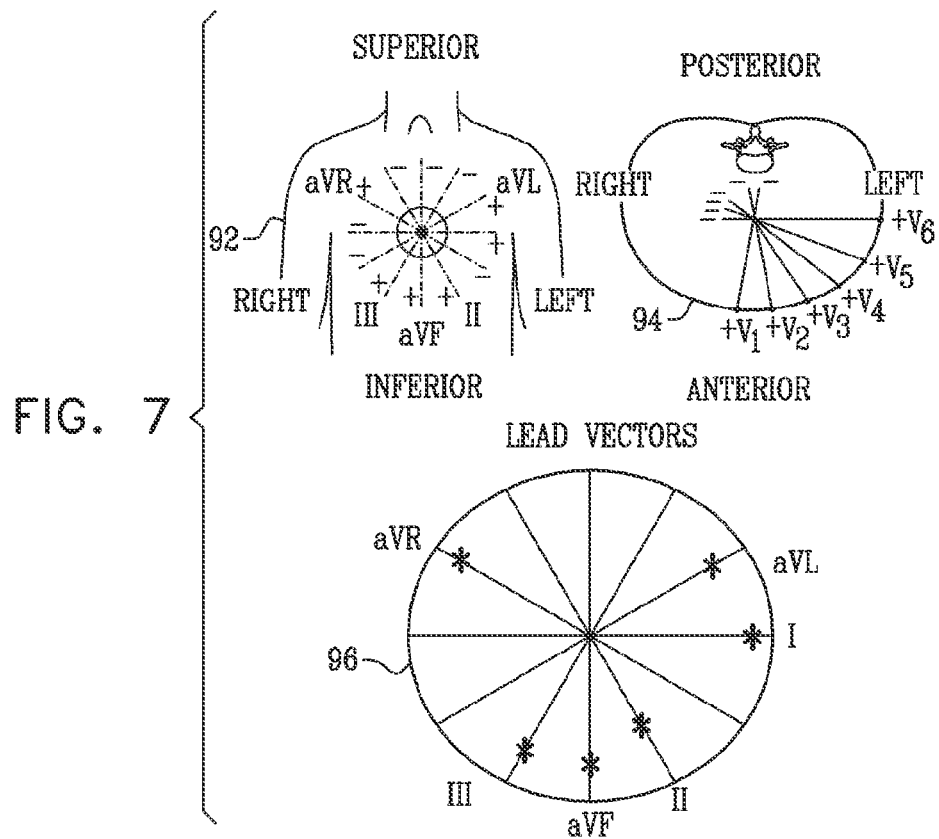
FIG. 7 is a composite graphic display of correlation results in accordance with a disclosed embodiment of the invention.

Reference is now made to FIG. 7, which is a composite graphic display of correlation results in accordance with a disclosed embodiment of the invention. This display is typically prepared following performance of the methods disclosed above. Three ECG vector representations 92, 94, 96 are shown. Similarity results are indicated by asterisks on each vector. Negative correlations are marked on the negative side of the axis.

Template Construction

Templates are constructed from induced signals recording. As noted above, one records approximately 2.5 seconds of 12-lead body surface ECG recording during the setup phase, and independent of the status of any internal catheters to ensure an accurate visual framework for mapping diagnostic procedures. These signals are not associated with any catheter location.

As noted above, it is desirable to have a beat buffer for IS signals, similar to the current beat buffer for the points, i.e., 10 beats are frozen with each signal, the user can select the beat to save. After saving, the non-selected beats are lost. While typically done by a human operator, in some embodiments the selection may be done automatically using conventional morphologic analysis techniques, e.g., pattern recognition.

The time of acquisition is recorded with the IS signal (hh:mm).

Figure 8:
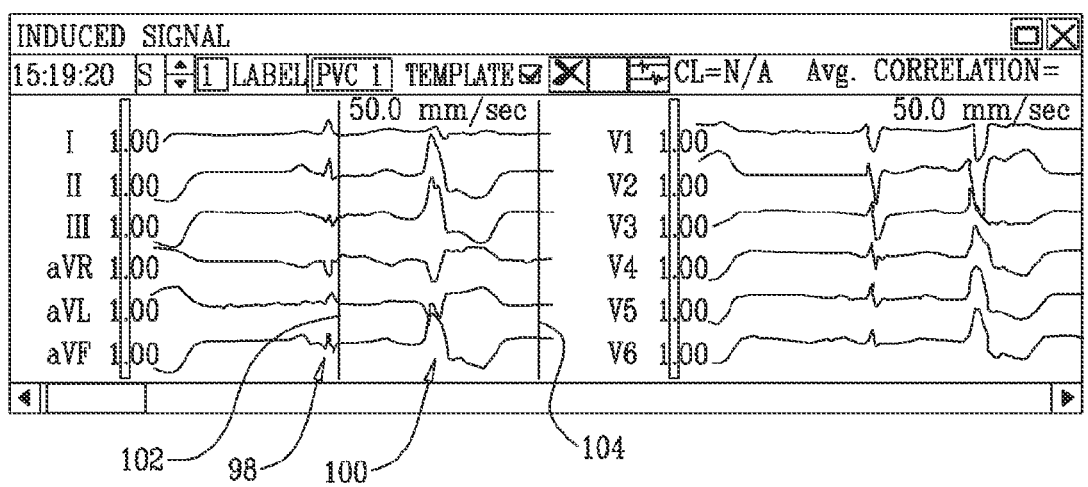
FIG. 8 is an exemplary 12-lead tracing showing an induced signal, in accordance with a disclosed embodiment of the invention.

Typically, about five induced signals are recorded. A maximum of 40 IS may normally be recorded. Reference is now made to FIG. 8, which is an exemplary 12-lead tracing showing an induced signal, in accordance with a disclosed embodiment of the invention. A stimulus is referenced by an arrow 98 and a resulting ventricular complex indicated by an arrow 100. A window of interest is framed by vertical lines 102, 104.

Reference is now made to FIG. 9, which is a series of tracings similar to FIG. 8, with superimposition of two series of signals to visually indicate correlations, in accordance with a disclosed embodiment of the invention.

For the first IS signal, the user marks the complex of interest with horizontal calipers or a similar tool. The default is from the first peak of the lead II (positive or negative) +/−150 ms. If the first peak on lead II is less than 150 ms from the beginning of the data recording, the next peak is used. Alternatively, the complex of interest can be identified automatically using conventional peak recognition techniques in the art, after which the operator confirms the result.

The first IS signal is automatically marked as a template.

Each additional IS is automatically checked for similarity with the window of interest of all existing templates. Similarity is checked with cross correlation for each lead separately, and for all leads on the same section of the signal (from a timing point of view).

There is a user defined IS correlation threshold (between 0 and 1) and a user-defined minimum number of leads (Min-ISL). The default ISCT=0.9; default Min-ISL=10-11. Each lead's correlation is tested against the ISCT.

If at least Min-ISL have correlation coefficients that are greater than ISCT, the signals are considered similar and the new IS is not marked as a template.

Otherwise, the new IS is marked as a template. The default area of interest is that found by the correlation, and it can be changed by the user.

The average correlation coefficient is calculated and presented.

The user may override the automatic template assignment (i.e., if the SW marked it as a template, it may be unmarked, and vice versa).

Each IS can have a unique label of four or fewer characters. The label will not be removed if the IS is selected or deselected as a template. If ISCT or Min-ISL are changed while acquiring templates, the system recalculates correlations and marks the IS as templates accordingly.

Manual selections (or deselections) by the user may be saved.

Pace-Mapping Procedure

One records approximately 2.5 seconds of 12-lead body surface ECG without the need to "freeze" a point of the tracing in time.

It is desirable to have a beat buffer for PM signals, similar to the current beat buffer for the points, i.e., 10 beats are frozen with each signal. The user can select the beat to save. After saving, the non-selected beats are normally discarded.

The time of acquisition is recorded with the PM signal.

One associates the PM signals with a point, i.e., a location. If no point is selected, the PM is associated with the last point acquired.

A PM tag is added to the point with a PM associated with it. If CardioLab® integration is available, this tag is also sent to the CardioLab system. The above-noted beat buffer from the same or a different study may be stored on the CardioLab (or similar) system, and can be imported when required.

Beside each PM tag a label indicates to which template it best correlates.

The PM tag label is shown independently to the other tag labels. PM signals are numbered consecutively.

Only one PM signal may be associated with each point. A PM signal cannot be associated with more than one point.

When a point is copied or moved to another map, all its links are copied with it.

When a point is deleted, all the links for this point are deleted. If the point is restored, the links need to be re-established automatically.

PM signals are normally saved with the study.

PM 12 lead signals may be printed. The name of the patient, date and time of acquisition are printed with it.

Functional Maps

In one aspect of the invention maps are displayed showing in which correlations of pace-mapped locations and IS templates are indicated by a color scale. Construction of functional maps may be accomplished using known methods; for example, those taught in the above-noted U.S. Pat. Nos. 6,226,542, and 6,301,496.

Figure 10:
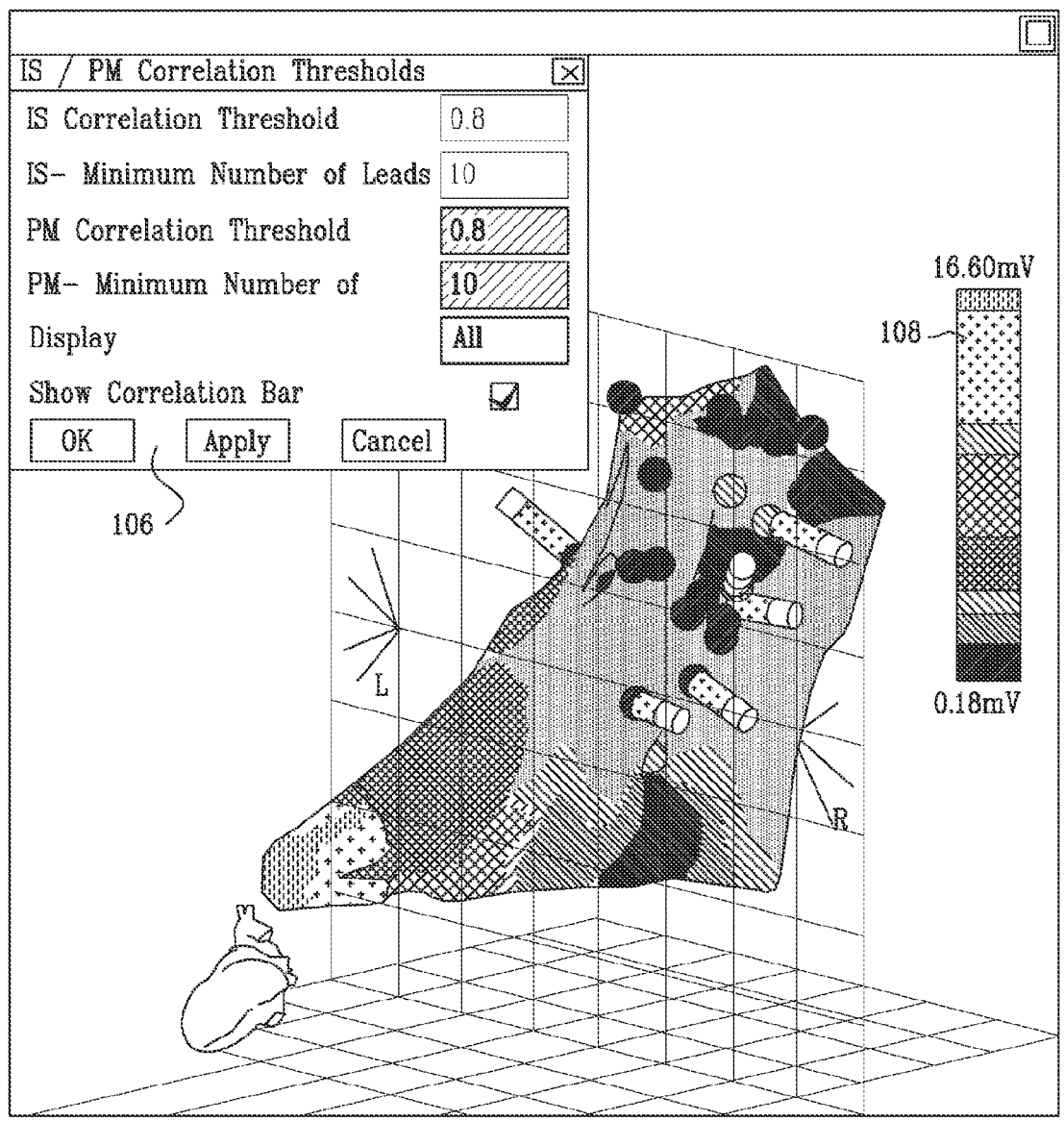
FIG. 10 is a functional map of the left ventricle of a heart, illustrating cross-correlation between a pace-mapped signal and an induced signal in accordance with a disclosed embodiment of the invention.

Reference is now made to FIG. 10, which is a functional map of the left ventricle of a heart, illustrating cross-correlation between a pace-mapped signal and an induced signal in accordance with a disclosed embodiment of the invention. Correlation parameters and measurements are shown in a dialog box 106 in the upper left portion of the figure. The degree of cross correlation may be interpreted with reference to a color scale 108. On the correlation map, a pacing point is defined as the best average correlation value between induced signals and a pace-mapped signal.

Superimposition of a correlation map with a CARTO map used to define a scarred area assists the operator in choosing a site for ablation, and choosing the order of points to ablate.

Figure 11:
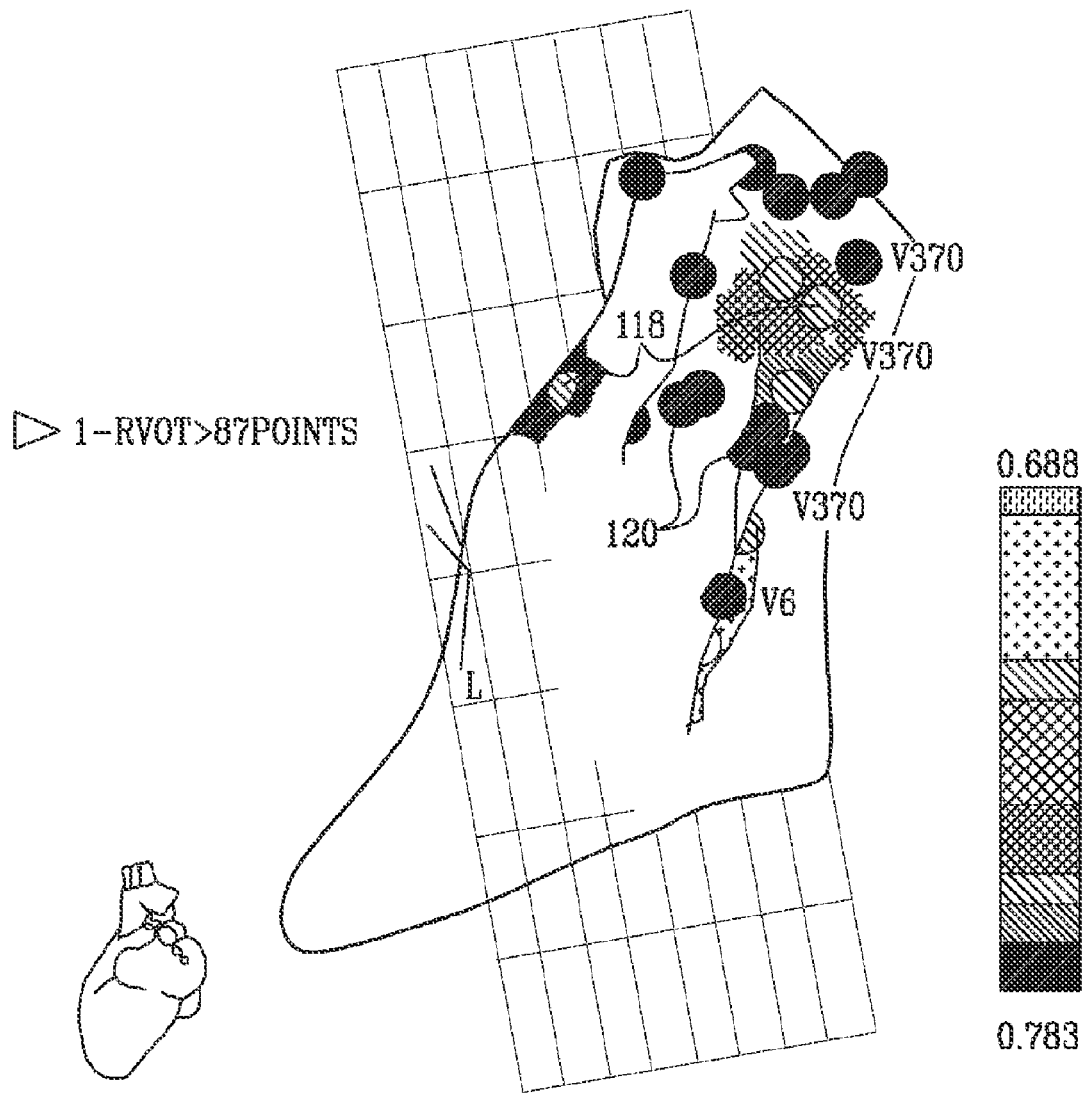
FIG. 11 is another functional map of the left ventricle shown in FIG. 10, in accordance with a disclosed embodiment of the invention.

Reference is now made to FIG. 11, which is a functional map of the left ventricle shown in FIG. 10. Here color-coded balls 118, also known as "point tags", represent pace-mapped points that exceed the correlation threshold of significance. Differently color-coded balls 120 represent points designated for ablation. Alternatively, other types of markings may be substituted for the balls 118, 120.

Principal Component Analysis

In the above-noted PCA correlation method, the algorithm objective is to locate similarity between a first set of signals—identified with the relevant tachycardia (training set) and a second set of body surface ECG leads signals, while pacing from the heart (tested set).

The training set is used to generate a set of signals that encapsulate most of the information. Principle component analysis and optionally Independent Component Analysis (ICA) are used to generate a set of base functions. Both of these techniques are well-known computational methods, and are therefore not further discussed herein. These functions are validated to span the whole instances of the training set where the input signal is estimated as with good enough accuracy. In order for PCA and ICA to operate optimally, preprocessing is performed that cuts the signals into segments that represent only one cycle of the ECG. A scaling and offset removal transfers the sections into a more uniform signal space, which results in the set. Using the base functions encapsulates most of the information, while rejecting sections of sparse morphology.

To look for correlation between a test set and the training, the test set passes the through above-described preprocessing procedure, and sections are generated. The base functions are then used to estimate the coefficients that best represent the signal.

If the representation is not accurate enough, it is assumed to be non-correlated with the training set. Otherwise, a correlation is made over all the leads simultaneously. In this way the regulation of the base function improves the observability between signals with different morphology by excluding sections that are sparse and produce a low correlation for corresponding signals. On the other hand, it causes a much smaller correlation in unlike signals due to amplification of the common dissimilar morphology.

Alternate Embodiment 1

Referring again to FIG. 1, in this embodiment a cardiologist paces the heart at different locations in the ventricle while observing a 12-lead body-surface ECG, as described above. Upon observing a suspicious pattern in the ECG (containing tachycardia or other arrhythmic components), the cardiologist signals the system 10 to mark the time interval containing the suspicious pattern as well as the pacing location at which the pattern occurred. Multiple intervals may be marked in this manner. The system 10 then learns the characteristics of the suspicious ECG pattern.

Subsequently, the cardiologist scans the pacing catheter over the inner wall of the ventricle, while the system 10 monitors and analyzes the ECG signals to detect further occurrences of the pattern it has learned. The system 10 marks any locations at which the pattern recurs as possible VT foci. The cardiologist may then ablate these foci or conduct further studies around the focal locations.

The system 10 may learn the pattern of the local electrograms sensed using the catheter 14 at the suspected VT foci that are marked by the cardiologist.

The catheter signal at different locations in the ventricle may then be analyzed for recurrence of this local electrogram pattern, in addition to or instead of the ECG.

Figure 12:
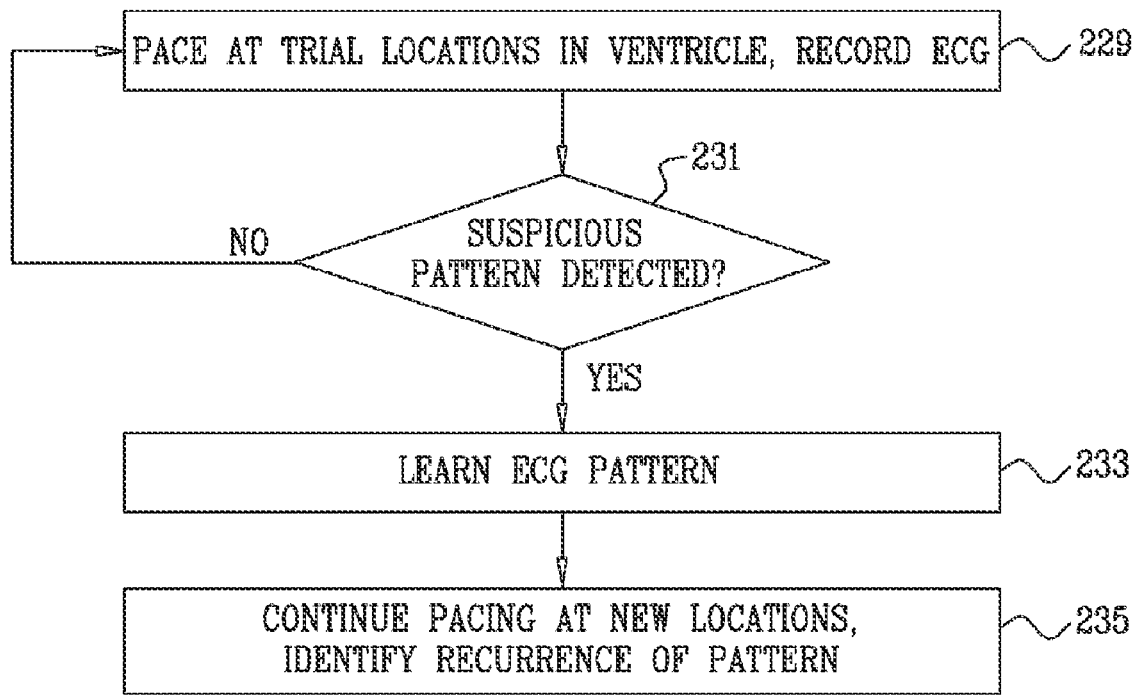
FIG. 12 is a flow chart of a method for identifying abnormal ECG patterns such as VT patterns in accordance with an alternate embodiment of the invention.

Reference is now made to FIG. 12, which is a flow chart of a method for identifying abnormal ECG patterns such as VT patterns in accordance with an alternate embodiment of the invention. At initial step 229, pacing is performed at trial locations, as described above.

Control now proceeds to decision step 231, where it is determined if a suspicious pattern has been detected. If the determination at decision step 231 is negative, then control returns to initial step 229 and pacing continues at new locations. VT patterns that are identified or automatically identified and confirmed by expert cardiologists may be stored in a library of patterns. This library may then be distributed to other cardiologists for their use in automatic identification and treatment of possible VT foci at decision step 231.

If the determination at decision step 231 is affirmative, then control proceeds to step 233, where the new pattern is learned automatically.

Subsequently, at final step 235, which may be performed, for example, after an attempt at ablation, pacing is repeated at new locations in the heart, in order to determine whether the abnormal pattern persists or has recurred.

In this embodiment, a reference signal is obtained as described above. Referring again to FIG. 1, the processor 23 displays the measured ECG signals to a physician. The physician identifies an exemplary occurrence of a pattern of interest in the displayed signals and indicates the time interval containing the pattern to the system. The methods and systems of this embodiment relieve the physician of the tedious and time-consuming task of manually scanning lengthy ECG signal traces to detect a pattern of interest. Moreover, these methods and systems are based on automatic analysis of an exemplary pattern and not on an explicit quantitative definition of the pattern, which is sometimes difficult to specify.

The processor 23 operates as a pattern processor, which analyzes the time interval and produces a characteristic signature of the pattern. Typically, the processor divides the time interval into multiple segments along the time axis and calculates a signal characteristic in each of the segments. The processor uses the sequence of signal characteristics of the different segments as the pattern signature. For example, the signal characteristic may comprise an indication whether the signal increases or decreases in the segment.

The processor 23 scans the ECG signal and detects other occurrences of the pattern of interest. The processor 23 identifies time intervals, in which the signal matches the pattern signature. The pattern signature may comprise a string, in which the signal characteristic value of each segment is represented by a corresponding character. In these embodiments, the processor detects occurrences of the pattern using a string matching process. The detected pattern occurrences are marked and displayed to the physician.

Additionally or alternatively, the pattern of interest may be provided externally, such as from a library of characteristic ECG patterns. The system 10 can also be used to define a library of patterns that have been found to be associated with certain types of pathologies or events. This library may be distributed to other cardiologists or systems for use in processing ECG signals gathered from other patients.

Figure 13:
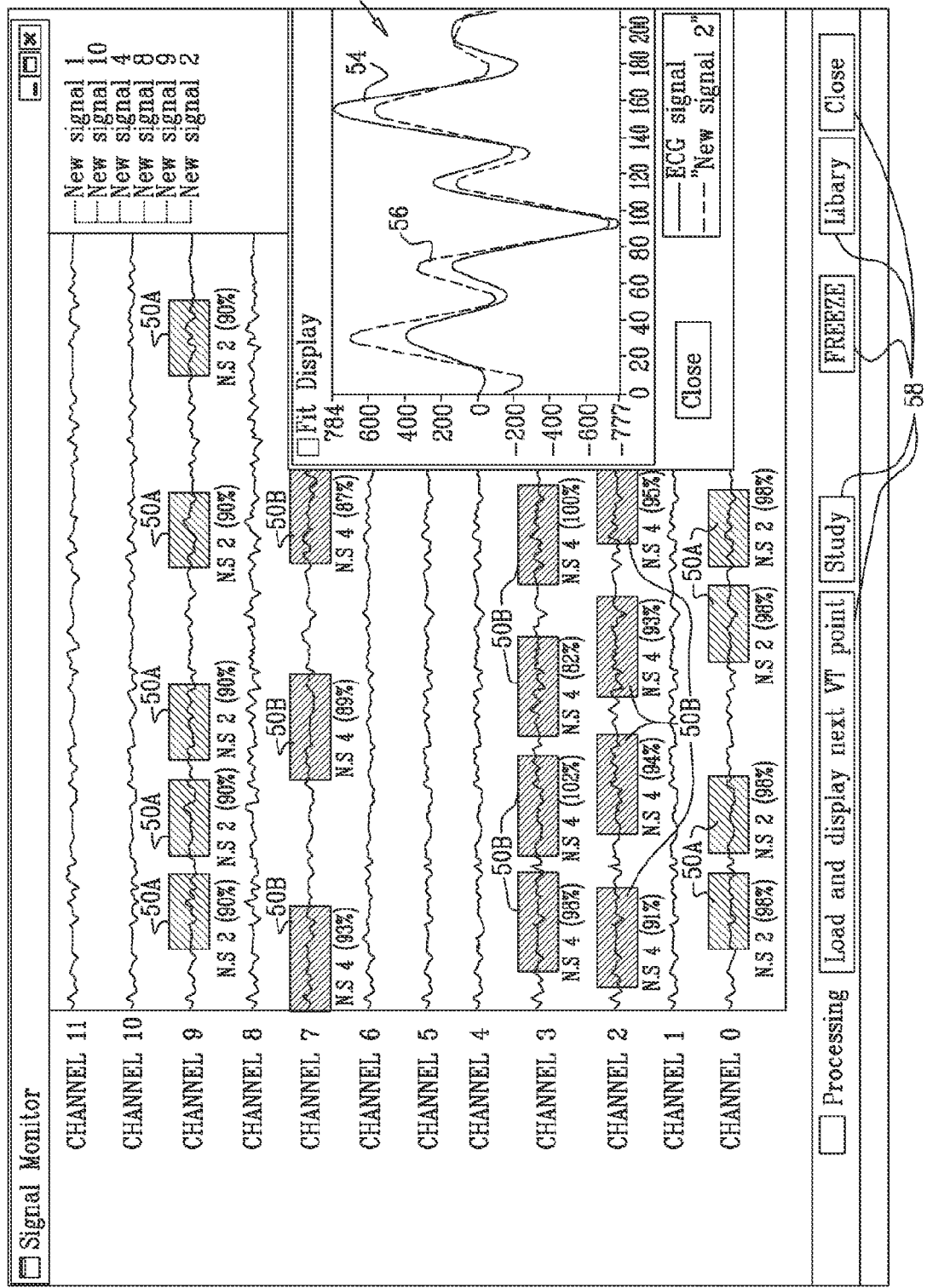
FIG. 13 is a diagram that schematically illustrates an exemplary display of an ECG signal analysis system, in accordance with an embodiment of the present invention.

Reference is now made to FIG. 13, which is a diagram that schematically illustrates an exemplary screenshot display of system 10, as displayed to the physician on display 44, in accordance with an embodiment of the present invention. The figure shows twelve ECG signals originating from twelve electrodes 32 (FIG. 1). Two patterns of interest, denoted "new signal 2" and "new signal 4" have been previously defined by the physician. Processor 23 simultaneously detects occurrences of the two patterns in the ECG signals. In the present example, the detected occurrences are marked using shaded areas on the displayed ECG signals. Alternatively, the occurrences can be marked using any other suitable indication, such as using different color, icons or highlighted areas.

Occurrences of the "new signal 2" pattern are denoted 50A and marked with a certain shading pattern, while occurrences of the "new signal 4" pattern are denoted 50B and marked with a different pattern. The quality or confidence level of the match is indicated as a percentage next to each occurrence.

A fitting window 52 shows the matching of a particular occurrence to the pattern of interest. Curves 54 and 56 respectively show the pattern and one of the occurrences, laid one on top of the other. Various controls 58 enable the physician to freeze the displayed ECG signals, select a particular occurrence, add another pattern of interest, etc. In alternative embodiments, any other suitable man-machine interface features and methods can be used.

ECG Signal Analysis Method

Figure 14:
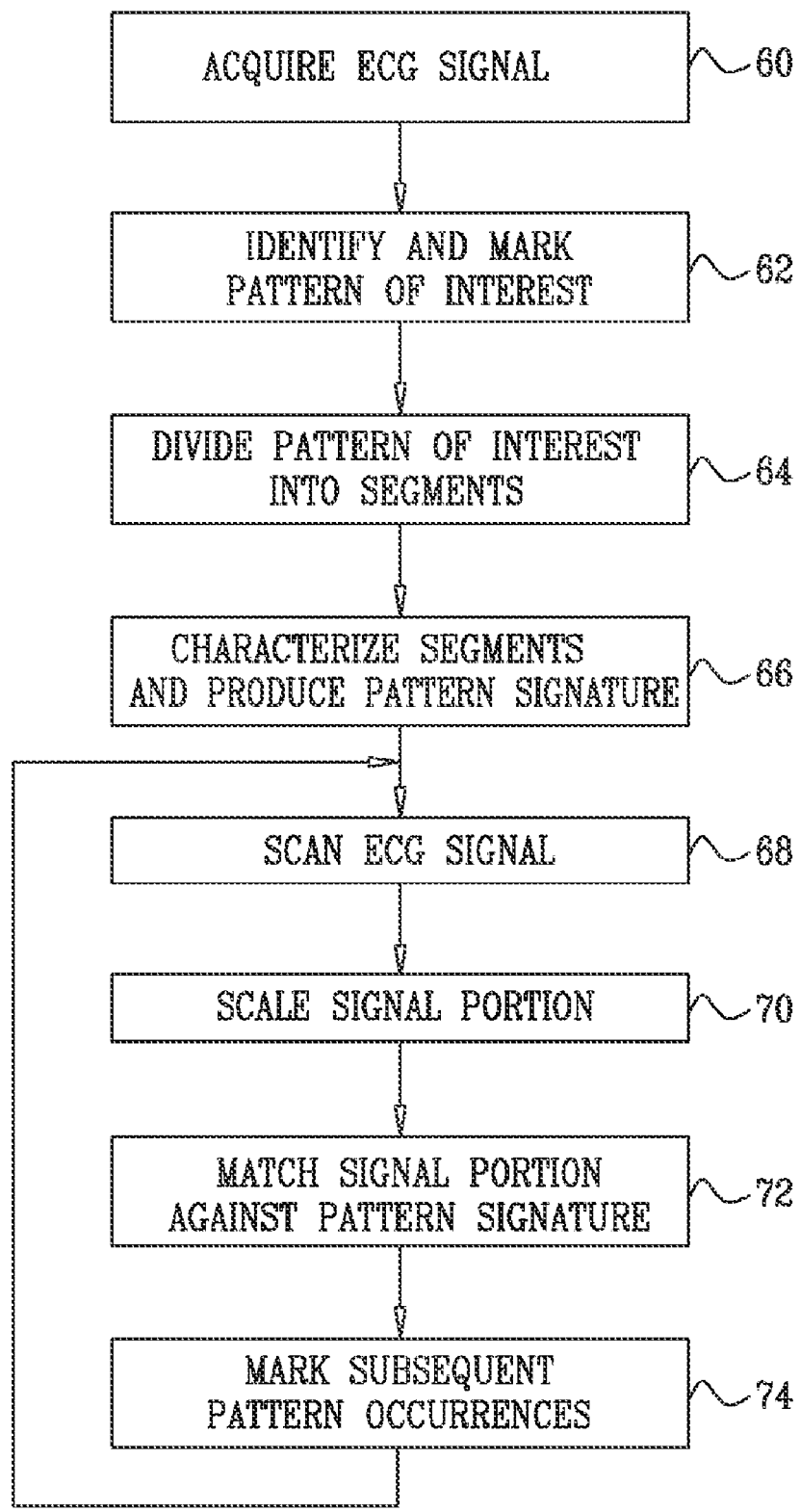
FIG. 14 is a flow chart that schematically illustrates a method for analyzing ECG signals, in accordance with an embodiment of the present invention.

Reference is now made to FIG. 14, which is a flow chart that schematically illustrates a method for analyzing ECG signals, in accordance with an embodiment of the present invention. The method begins with system 10 acquiring an ECG signal, at an acquisition step 60. The acquired signal is displayed to the operator, either in real time or off-line. The operator identifies and marks a time interval that contains a pattern of interest, at a pattern indication step 62.

Processor 23 divides the time interval marked by the operator into multiple segments, at a segmentation step 64. The pattern processor characterizes the ECG signal in each of the segments and produces a pattern signature based on the sequence of signal characteristics, at a signature generation step 66. For example, the processor may determine, for each segment, whether the signal increases or decreases along the segment. The processor can then generate a sequence of "ascending" and "descending" indications, which is used as a characteristic signature of the pattern of interest. In these embodiments, the number of segments is typically selected with sufficient resolution, so that the signal inside each segment is likely to be monotonous.

Additionally or alternatively, the processor 23 can use any other suitable parameter in order to characterize the different segments, such as the positive or negative slope of the signal within the segment. In some embodiments, processor 23 represents the pattern signature as a string, in which each segment is represented by a character. For example, a segment in which the signal increases can be represented by a "U" character. A segment in which the signal decreases can be represented by a "D" character. The characters representing the segments are then concatenated to form a string such as "UDDUUDUDU . . . UUD", which is used as a signature.

In some embodiments, processor 23 measures one or more scaling parameters of the ECG signal in the marked time interval. These scaling parameters are stored together with the signature and are later used for matching other occurrences of the pattern. For example, the mean amplitude of the signal can be used as a scaling parameter. Additionally or alternatively, the processor may calculate a spectrum of the pattern of interest and determine one or more dominant frequencies in the spectrum. The dominant frequencies can be used as scaling parameters.

Having generated the pattern signature, processor 23 scans the ECG signal and attempts to detect other occurrences of the pattern of interest, at a scanning step 68. Depending on the system configuration used, processor 23 may monitor real time or buffered ECG measurements as they are acquired, or scan in an off-line manner through a body of previously measured ECG signals.

The processor scales a portion of the scanned ECG signal responsively to the scaling parameters of the pattern of interest, at a scaling step 70. For example, the processor may normalize the mean amplitude of the scanned signal to match the mean amplitude of the pattern of interest. As another example, the processor may perform spectral scaling of the scanned signal, so that its dominant frequencies match the dominant frequencies of the pattern of interest. Spectral scaling can be viewed as scaling (i.e., stretching or compressing) the time axis of the scanned signal with respect to the time axis of the pattern of interest. The processor may compute a fast Fourier transform (FFT) of the scanned signal portion for this purpose.

Processor 23 attempts to find intervals in the scanned ECG signal that match the pattern signature, at a matching step 72. For example, when the pattern of interest is represented using a string, the processor divides the scanned and scaled signal portion into segments, characterizes each segment and assigns a character to each segment. The scanned signal portion is thus represented by a long string of characters. Then, the processor attempts to find the sub-string that represents the pattern signature in the string that represents the scanned signal portion. Any suitable string matching process known in the art can be used for this purpose. Each match is considered to be an occurrence of the pattern in the scanned signal.

Processor 23 marks the detected occurrences on display 44, at an occurrence indication step 74. Typically, the processor marks the time intervals that are detected as pattern occurrences. Since the processor may search for several patterns simultaneously, the pattern being detected is indicated next to each occurrence. In some embodiments, each occurrence is also given a unique name or number that is displayed. The processor may also display a confidence level or a quality metric of the match next to each detected occurrence.

Although the description of this embodiment mainly addresses identifying patterns in an ECG signal, the principles of the present invention can also be used for detecting patterns in other physiological signals, such as electroencephalogram (EEG) and respiratory signals.

Alternate Embodiment 2

In this embodiment, instead of using a conventional body surface electrocardiogram, electrocardiographic signals are captured using remote interrogation of implanted patient devices, typically intracardiac devices (ICDs) such as defibrillators, cardioverters, and pacemakers. Such devices may be provided with memories for storing signals that reflect cardiac events. Historic signals are downloaded as recorded (historic) signals or in realtime to a processing system and compared with induced signal patterns (a first type of realtime signal) and with pace mapped patterns (a second type of realtime signal). The historic signals may include spontaneous episodes of ventricular tachycardia. In some embodiments, the signals may be transmitted to and stored on a server and then transferred to the processing system. A suitable intracardiac device for capturing the signals is the Medtronic InSync® ICD. Other suitable devices are commercially available.

Figure 15:
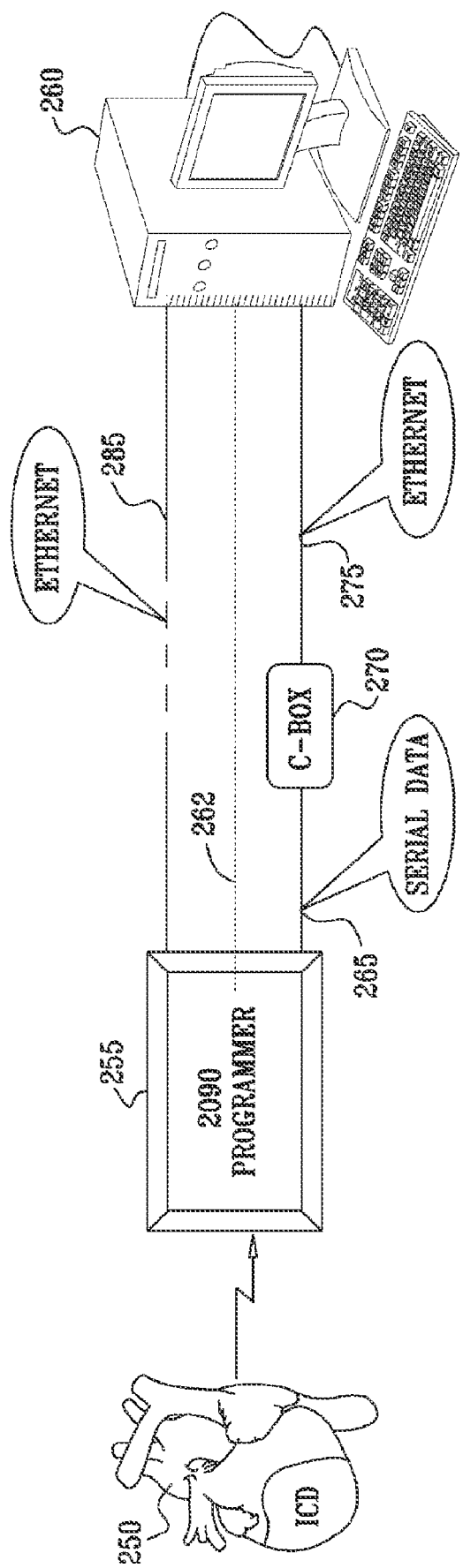
FIG. 15 is a pictorial diagram of an arrangement for remotely identifying abnormal ECG patterns in accordance with an alternate embodiment of the invention.

Reference is now made to FIG. 15, which is a pictorial diagram of a representative arrangement for remotely identifying abnormal ECG patterns in accordance with an alternate embodiment of the invention. Other conventional methods of transferring data between an ICD 250 and processing system 260, for example USB communications or even removable storage media. Alternatively, the communication may be achieved by a dedicated device that is adapted to directly interrogate the ICD 250.

To capture a realtime electrocardiographic signal, the ICD 250 band-pass filters (e.g., 2.5-100 Hz) and samples the signals at 128-256 Hz. A sampling rate of 256 Hz or higher is preferable. A processing and programming device 255 is used to receive the sampled signal, and then upsampled. A first upsampling to 400 Hz and a second to about 7 kHz are suitable. A Medtronic 2090 programmer may be used as the device 255 for interrogation of the ICD 250 and wired or linked by wireless telemetry to the processing system 260, which can be the above-noted CARTO XP EP Navigation and Ablation System. Different combinations of wired and wireless links between the ICD 250, the device 255 and the processing system 260 may be used.

According to one alternative, the upsampled signal is then converted into an analog signal 262, for example using a model 7808 digital-to-analog converter (DAC) (not shown), which is then telemetered to the processing system 260.

In another alternative, the upsampled signal is converted from serial data 265 by a converter 270 (C-box) to a digital format 275 suitable for network transmission, for example the Ethernet protocol. The processing system 260 is provided with a suitable receiver for accepting the Ethernet signals (or analog signals). This method has the advantage of using an industry standard, but does present time synchronization issues. In the current embodiment, the Ethernet protocol can concurrently support up to 10 ECG channels. Command exchange between the processing system 260 and the device 255 requires a separate channel 285.

The signals received by the device 255 are processed by processing system 260 for comparison with another set of electrocardiographic signals captured by the ICD 250 during a current or previous pace mapping session. The results may be correlated with IS signals captured by the ICD leads or with VT morphologies in ICD-stored events, captured from the ICD 250 or from a different source. Alternatively, the signals can be correlated with a library of patterns, both alternatives being described above.

In some embodiments, the location at which correlation and analysis is done may even be remote from the site at which pace-mapping is done. In such case, the pace-mapped signals described above may also be transmitted to the analysis location using the same or a different communications protocol.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. An apparatus for locating an arrhythmogenic abnormality in a heart of a living subject, comprising:
    a mapping catheter operative for stimulating said heart at multiple locations endocardially or epicardially; and detecting respective sets of pace-mapped electrocardiographic signals at respective locations of said catheter, said catheter having a position sensor;
    a position processor programmed to receive position signals from said position sensor and operative for determining said respective locations of said catheter; and wherein said mapping catheter is used for creating a functional map;
    a display for displaying said functional map;
    a pattern processor, programmed for detecting an abnormal electrocardiographic signal pattern in said sets of pace-mapped electrocardiographic signals indicative of an arrhythmogenic focus or pathway and marking said abnormal electrocardiographic signal pattern on said functional map on said display;
    memorizing said pattern; and
    subsequently automatically identifying a new instance of said pattern and marking said new instance of said pattern on said functional map on said display when recording new electrocardiographic signals.

2. The apparatus according to claim 1, wherein said new electrocardiographic signals are obtained from an implanted intracardiac device and is transmitted to an analysis location in realtime.

* * * * *